(12) United States Patent
Boughorbel (10) Patent No.: US 9,901,430 B2
(45) Date of Patent: Feb. 27, 2018

(54) ORAL HEALTHCARE SYSTEM AND METHOD OF OPERATION THEREOF

(71) Applicant: KONINKLIJKE PHILIPS N.V., Eindhoven (NL)

(72) Inventor: Sabri Boughorbel, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/036,485

(22) PCT Filed: Apr. 28, 2015

(86) PCT No.: PCT/IB2015/053067
§ 371 (c)(1),
(2) Date: May 13, 2016

(87) PCT Pub. No.: WO2015/177661
PCT Pub. Date: Nov. 26, 2015

(65) Prior Publication Data
US 2017/0056146 A1     Mar. 2, 2017

Related U.S. Application Data

(60) Provisional application No. 62/001,101, filed on May 21, 2014.

(51) Int. Cl.
*A61C 19/04*     (2006.01)
*A61C 17/22*     (2006.01)
(Continued)

(52) U.S. Cl.
CPC .............. *A61C 17/221* (2013.01); *A46B 9/04* (2013.01); *A46B 15/0004* (2013.01);
(Continued)

(58) Field of Classification Search
CPC .............. A61C 19/04; A61C 2204/005; A46B 15/0002
See application file for complete search history.

(56) References Cited

U.S. PATENT DOCUMENTS 3,297,021 A * 1/1967 Davis .................. A61B 5/0002
340/870.16
4,435,163 A * 3/1984 Schmitt ................ G09B 23/283
434/263
(Continued)

FOREIGN PATENT DOCUMENTS

JP     2013097440 A     5/2013
WO    2014016718 A1    1/2014

OTHER PUBLICATIONS

Li et al: "Sensor-Embedded Teeth for Oral Activity Recognition": ACM, ISWC'13, Sep. 9-12, 2013, 4 Page Article.

*Primary Examiner* — Ralph Lewis (57) ABSTRACT

A personal care system (100) includes a personal care appliance (107) having a body (141), and at least one cavity (109). The body may be configured to receive a cleaning tool (111) at one end and may include at least one controller (122) which may be situated within the at least one cavity. The controller may be configured to: determine whether a personal care mode is activated; obtain sensor information from at least one tooth-based sensor (152) of a tooth portion (112), when it is determined that a personal care mode is activated; and transmit the sensor information to at least one of a remote server (102) and a base portion (132).

14 Claims, 3 Drawing Sheets

(51) Int. Cl.
*A46B 15/00* (2006.01)
*A46B 9/04* (2006.01)
*A61B 5/00* (2006.01)
*A61B 5/01* (2006.01)
*A61B 5/145* (2006.01)
*A61C 1/00* (2006.01)
*A61B 90/00* (2016.01)

(52) U.S. Cl.
CPC ...... *A46B 15/0012* (2013.01); *A46B 15/0014* (2013.01); *A61B 5/0031* (2013.01); *A61B 5/01* (2013.01); *A61B 5/14532* (2013.01); *A61B 5/14539* (2013.01); *A61B 5/14546* (2013.01); *A61B 5/4547* (2013.01); *A61B 5/682* (2013.01); *A61C 1/0015* (2013.01); *A46B 2200/1066* (2013.01); *A61B 2090/064* (2016.02); *A61B 2560/0209* (2013.01); *A61B 2560/0456* (2013.01); *A61B 2562/0204* (2013.01)

(56) References Cited

U.S. PATENT DOCUMENTS

| | | | |
|---|---|---|---|
| 6,239,705 B1 | 5/2001 | Glen | |
| 6,536,068 B1* | 3/2003 | Yang | A46B 15/0002 15/105 |
| 6,786,732 B2* | 9/2004 | Savill | A46B 15/0002 434/263 |
| 8,337,213 B2* | 12/2012 | Puurunen | A46B 15/0006 434/262 |
| 8,649,543 B2 | 2/2014 | Abolfathi et al. | |
| 2007/0106138 A1* | 5/2007 | Beiski | A61B 5/682 600/349 |
| 2009/0317770 A1* | 12/2009 | Gatzemeyer | A46B 15/0002 433/215 |
| 2010/0014689 A1 | 1/2010 | Kassayan et al. | |
| 2012/0171657 A1* | 7/2012 | Ortins | A46B 9/04 434/365 |
| 2013/0278396 A1 | 10/2013 | Kimmel | |

* cited by examiner

ORAL HEALTHCARE SYSTEM AND METHOD OF OPERATION THEREOF

CROSS-REFERENCE TO PRIOR APPLICATIONS

This application is the U.S. National Phase application under 35 U.S.C. § 371 of International Application No. PCT/IB2015/053067, filed on Apr. 28, 2015, which claims the benefit of U.S. Provisional Patent Application No. 62/001,101, filed on May 21, 2014. These applications are hereby incorporated by reference herein.

The present system relates to an oral healthcare system and, more particularly, to an oral healthcare system which non-obtrusively acquires information for analysis, and a method of operation thereof.

Oral healthcare is an important element in personal care. While it is known that medical conditions of a user may be determined using an analysis of biologic samples obtained from a mouth of a user such as a saliva sample, these biologic samples are typically obtained using obtrusive methods such as by using a swab or the like to acquire the sample. This can cause user discomfort and can be inconvenient as the samples must typically be obtained by a medical professional to assure proper handling for analysis. Accordingly, because of the obtrusive and inconvenient collection methods used to obtain the biological samples, a user is unlikely to provide biologic samples on a periodic basis. Accordingly, embodiments of the present system overcome the disadvantages of prior art systems and methods.

The system(s), device(s), method(s), arrangements(s), user interface(s), computer program(s), processes, etc. (hereinafter each of which will be referred to as system, unless the context indicates otherwise), described herein address problems in prior art systems.

In accordance with embodiments of the present system, there is disclosed an electronic oral cleaning system which may include: a personal care apparatus (PCA) having a body with first and second ends and at least one cavity which may be situated between the first and second ends, the body may be configured to receive a cleaning tool at the second end and may include at least one controller which may be situated within the at least one cavity and which may be configured to: determine whether a personal care mode is activated; obtain sensor information from at least one tooth-based sensor of a tooth portion, when it is determined that a personal care mode is activated, and transmit the sensor information to at least one of a remote server and a base portion.

It is also envisioned that the PCA may further include at least one actuator which may be coupled to the cleaning tool and which may be controllably driven by the controller when the personal care mode is activated. The actuator may generate a force which may drive the cleaning with a desired motion. It is also envisioned that the sensor information may include information related to at least one of temperature, ph level, bacterial levels, presence of a target bacterium, audio information, force information, and glucose level. It is further envisioned that the at least one controller may be further configured to establish communication with the at least one tooth-based sensor using a low-energy wireless communication method. Moreover, the at least one controller may transmit the sensor information to the base portion when it is determined that a charging mode is activated. It is also envisioned that the base portion may be configured to receive the personal care apparatus and may include at least one controller configured to receive the sensor information and transmit the sensor information to the remote server. It is also envisioned that the remote server may include at least one processor configured to receive the transmitted sensor information and analyze the sensor information. The remote server may further transmit results of the analysis to at least one registered address of a user.

In accordance with yet other embodiments of the present system, there is disclosed a method of obtaining sensor information from at least one tooth-based sensor of a tooth portion by a personal care apparatus (PCA) having a body with at least one actuator and an oral cleaning tool coupled to the at least one actuator, the method performed by at least one controller of the PCA. The method may include one or more acts of: determining whether a personal care mode is activated; obtaining sensor information from the at least one tooth-based sensor, when it is determined that a personal care mode is activated; and transmitting the sensor information to at least one of a remote server and a base portion. It is also envisioned that the method may include an act of driving the at least one actuator to reciprocally drive the oral cleaning tool when the personal care mode is activated. Moreover, the sensor information may include information related to at least one of temperature, ph level, bacterial levels, presence of a target bacterium, audio information, force information, and glucose level. In accordance with some embodiments, the method may include an act of establishing communication with the at least one tooth-based sensor using a low-energy wireless communication method. It is also envisioned that the method may include an act of transmitting the sensor information to the base portion is performed when it is determined that a charging mode is activated. It is further envisioned that the act of transmitting the sensor information may further include acts of: receiving the sensor information at the base portion; and transmitting, by the base portion, the sensor information to the remote server. In accordance with some embodiments, the method may further include an act of analyzing the sensor information by the remote server. Moreover, the method may include an act of transmitting, by the remote server, results of the analysis to at least one registered address of a user.

In accordance with yet other embodiments of the present system, there is disclosed a non-transitory computer readable medium which may include computer instructions which, when executed by a processor, may configure the processor to control operation of an oral cleaning apparatus having a body portion and an oral cleaning tool extending from the body portion, the oral cleaning tool coupled to an actuator, by performing one or more acts of: determining whether a personal care mode is activated; obtaining sensor information from at least one tooth-based sensor of a tooth portion, when it is determined that a personal care mode is activated, and transmitting the sensor information to at least one of a remote server and a base portion.

It is also envisioned that the processor may be further configured to perform an act of driving the at least one actuator to reciprocally drive the oral cleaning tool when the personal care mode is activated. Moreover, the in accordance with some embodiments, the sensor information may include information related to at least one of temperature, ph level, bacterial levels, presence of a target bacterium audio information, force information, and glucose level. Further, in accordance with yet other embodiments, the processor may be further configured to perform an act of establishing communication with the at least one tooth-based sensor using a low-energy wireless communication method.

The present invention is explained in further detail in the following exemplary embodiments and with reference to the figures, where identical or similar elements are partly indicated by the same reference numerals, and the features of various exemplary embodiments being combinable. In the drawings.

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements.

Figure 1:
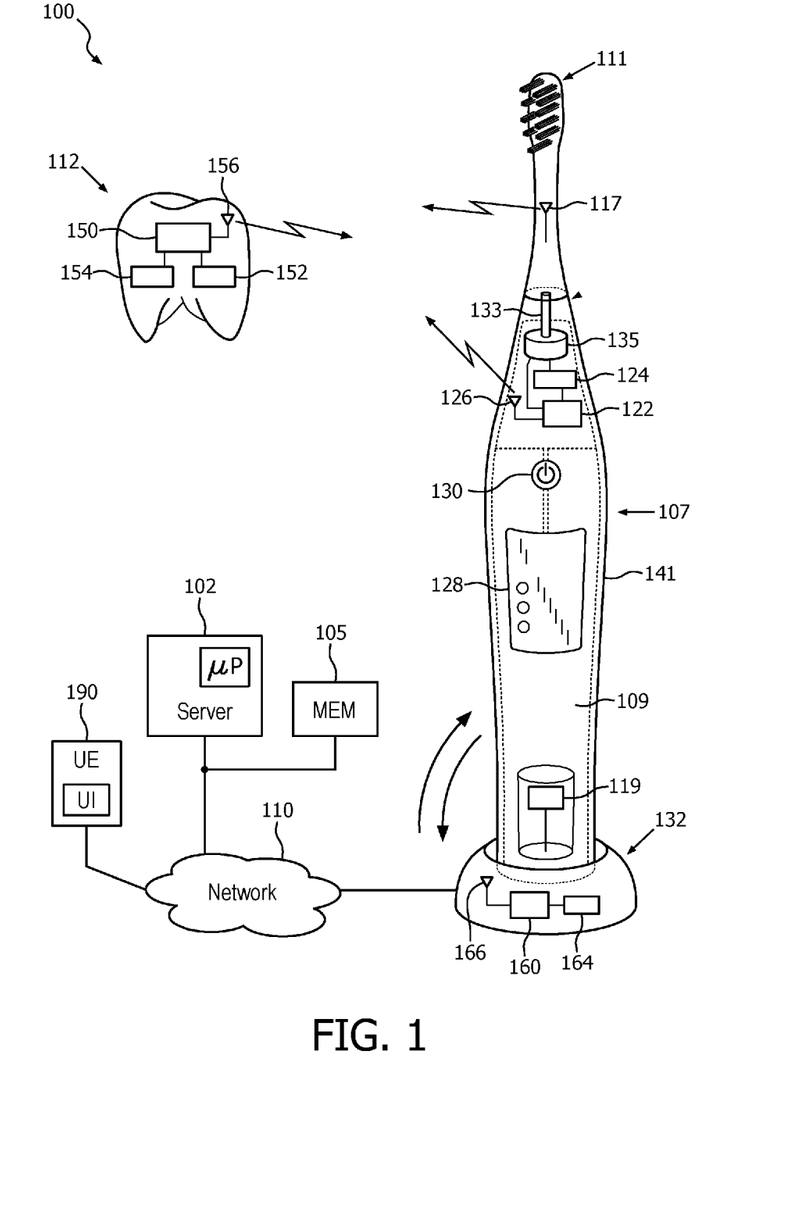
FIG. 1 shows a schematic block diagram of a portion of personal care system in accordance with embodiments of the present system.

FIG. 1 shows a schematic block diagram of a portion of personal care system 100 in accordance with embodiments of the present inventio. The personal care system 100 may include at least one of a server 102, a memory 105, user equipment 190, a network 110, a personal care apparatus (PCA) 107, a base 132, and a tooth portion 112 (e.g., a smart tooth or smart teeth) each of which may communicate with each other directly or via any suitable network such as the network 110. The PCA may be considered a smart toothbrush.

The network 110 may include any suitable network such as a wide area network (WAN), a local area network (LAN), a telephony network, a proprietary network, the Internet, an intranet, a Bluetooth™ network, an ad-hoc network, etc. Communication to and/or from the network may be performed using any suitable wired and/or wireless method or methods.

The memory 105 may store information for the system 100 such as operating information, information generated by the system 100 and/or user information. The memory 105 may include local and/or distributed memories.

The server 102 may include at least one processor and may control the overall operation of the system 100 and may include local and/or distributed processing portions (e.g., cloud-based). For example, the server 102 may include a cloud-based processing portion. The server 102 may obtain and/or be configured to obtain sensor information from at least one tooth portion 112 and analyze the sensor information to determine whether the sensor information may indicate whether a medical condition may be associated with the sensor information. The results of the determination may then be rendered on a display of the system and/or provided electronically to an address associated with the corresponding sensor information.

The user equipment (UE) 190 may include any suitable user device such as a personal computer (PC), a laptop computer, a tablet, a smart phone, or the like, which may include a user interface (UI) such as a speaker a display, a haptic device, etc., with which a user interacts with the system 100, if desired. Further, the UE 190 may include an input device such as a touchscreen, a keyboard, a mouse, a pointing device, etc. which may receive a user input. Accordingly, a user may interface with the user interface to select an operating mode of the PCA 107 from a plurality of operating modes as will be described elsewhere. Further, the UE 190 may communicate with the server 102 to send and/or receive information such as sensor information, parameter information, etc. Further, the UE 190 may generate a user interface (UI) with which the user may interact with the system 100 or portions thereof such as the PCA 107 to select an operating mode, if desired.

The PCA 107 includes a body 141 having at least one cavity 109 therein, a controller 122, a memory 124, at least one antenna 126, a power portion 119, and an actuator 135 situated within the at least one cavity 109. An output shaft 133 is coupled to the actuator 135 that has an output end protruding from the body 141 for receiving a tool 111 thereon. In accordance with some embodiments diversity transmission methods may be employed. For example, antenna 117 may be provided in addition to antenna 126 so as to provide for diversity transmission and/or reception. The antenna 117 may be situated in any suitable location such as in or on the tool 111. Further, in yet other embodiments, the antenna 117 may be substituted for antenna 126, if desired, and may be coupled to, and communicate with, the controller 122 similarly to the antenna 126. By using antenna 117 situated in or on the tool, the distance between a transmission antenna and the tooth portion 112 may be reduced.

The controller 122 may control the overall operation of the PCA 107 and may communicate with at least one of the memory 124, the at least one antenna 126, the actuator 135, the power portion 119, and one or more sensors.

The power portion 119 may provide power to operate the PCA 107 and may include at least one power source such as a battery, a capacitor, or the like. The power portion 119 may further include an inductive charging coil for inductively charging the at least one power source when the PCA 107 is placed in a charging position relative to the base 132.

The actuator 135 may be coupled to the output shaft 133 and may provide reciprocating electro-motive force as an output to drive the output shaft 133 in a desired direction (e.g. linearly and/or rotationally), speed, and/or frequency when activated. The actuator 135 may be driven by the controller 122 in accordance with one or more operating modes (e.g., brushing modes) which may set forth operating frequencies, amplitude, and/or patterns as may be selected by the controller 122 and/or user.

The tool 111 may receive the electro-motive force from the motive force from the actuator 135 which is suitable for hygienic care (e.g., brushing a user's teeth). The tool 111 may be a brush head which may include a plurality of brushes such as bristles, rubber wipers, etc.

The PCA may include an on-off switch 130, and a display 128 and/or a touch-sensitive input device to select various operating modes (e.g., functional modes) of the PCA 107 such as on on/off mode (generally on or off), a charging mode, a brushing mode (e.g., a gentle brushing mode, a regular brushing mode, a massage mode, etc.), a data transfer mode, a data acquisition mode, a tooth-sensor programming mode, etc. One or more of these modes may operate synchronously with each other, if desired. In accordance with some embodiments, it is envisioned that the user may set or select operating modes via a user interface generated and rendered by the UE 190 on a display of the system 100 such as on the display 128 or on another display of the system 100. The data transfer, data acquisition, and tooth-sensor programming modes are modes in which the PCA 107 may communicate with the tooth portion 112 as will be discussed below.

One or more operating modes of the PCA 107 may be actively selected (e.g., by selection of a hard or soft key by the user) and/or may be passively selected by the system 100 based upon sensor information obtained by the PCA 107 such as charge sensor information, acceleration sensor information, orientation information, pressure sensor information, etc. For the sake of clarity it will be assumed that the data transfer mode will be activated when the PCA 107 is determined to be charging (e.g., is or adjacent to the base 132 for charging) and the data acquisition mode may be activated when the PCA 107 is determined to be turned on.

The various operating modes and/or corresponding sensor information to activate the corresponding mode(s) may be stored in a table lookup and may be set by the system and/or user. For example, in accordance with some embodiments, the data acquisition mode and/or tooth-sensor programming mode may be activated when it is determined that the PCA 107 is turned on and pressure is applied to the tool 111 (this pressure may be indicative of a likelihood that the tool 111 applying a force against one or more teeth of a user). This may conserve energy as wireless communications may be performed only when it is likely that the tool 111 is adjacent to a user's tooth. In accordance with some embodiments, communication (e.g., for a data acquisition and/or for tooth-sensor programming) may be maintained until data is transmitted and/or received from the tooth portion 112 while the corresponding mode is still operative. For example, a data acquisition mode may be operative until all data is acquired or the PCA 107 is determined to be turned off (e.g., the actuator is turned off).

With regard to the tooth portion 112, the tooth portion may be a smart tooth and may include one or more of a controller 150 which may control the overall operation of the tooth portion 112, at least one sensor 152 which may generate corresponding sensor information and provide the sensor information to the controller 150 coupled thereto, a memory 154 which may store information of the tooth portion 112 such as operating instructions, operating parameters, and/or sensor information, and at least one antenna 156 which may wirelessly receive transmissions (such as information transmitted from the PCA 107 to the tooth portion 112) and may transmit information such as the sensor information and/or identification information which may identify the tooth portion 112. The tooth portion 112, or portions thereof, may be coupled to a surface (e.g., tooth enamel) within an oral cavity of a user using any suitable method. The tooth portion 112 may be read using any suitable method such as an RFID method.

Thus, a plurality of tooth portions 112 may be located in close proximity to each other and information transmitted by each of the tooth portions 112 may be distinguished from each other. The tooth portion 112 may further include an energy harnessing and/or storage portions. For example, in accordance with some embodiments, the at least one antenna 156 may further be operative to harness magnetic or radio-frequency energy (or the like) transmitted from the PCA 107 to the tooth portion 112. This harvested energy may then be stored in an energy storage device such as a capacitor, a battery, etc. within the tooth portion 112 for later use under the control of the controller 112.

The at least one sensor 152 of the tooth portion 112 may include various sensors as may be desired for a particular application. For example if audio information is desired, then the tooth portion 112 may include a power source to provide power, a microphone sensor to sense sound and provide this information to a controller for storage in a memory for later transmission to a reader in accordance with embodiments of the present system. However, if sensing of for example, bacterium is desired, one or more nanotransducers may be provided. Each nanotransducer may detect and/or be configured to detect one or more bacterium of interest. Further, each nanotransducer may include an ID which may identify the nanotransducer and/or any detected bacterium.

In yet another example, in accordance with some embodiments, the at least one sensor 112 may include one or more of a temperature sensor which may provide temperature information, an acidity sensor which may provide ph level information, a biometric sensor which may provide biometric information, a stress sensor to provide stress information (e.g., indicative of at least a portion of a force (in one or more directions) applied to a body of the corresponding tooth portion 112 which may be indicative of a user grinding teeth, eating, etc.), etc.

Other embodiments of the present system may further include sensors which may analyze fluids (e.g., saliva) to detect corresponding sensor information (e.g., particular protein types related to particular diseases) which may be analyzed to detect diseases such as diabetes, periodontitis, respiratory diseases, cardiovascular diseases (e.g., a heart attack or increased risk of a heart attack, etc.), cancer, etc. For example, continuous glucose monitoring (CGM) may be performed in accordance with sensor information obtained from any suitable glucose sensor (such as an implantable glucose sensor available from Sensonics™, Germantown, MD.) which may detect glucose levels of a user and form corresponding sensor information. This sensor information may then be analyzed using known methods locally or remotely and glucose level or range or levels may be determined such as by a controller of the system. It is further envisioned that one or more of the sensors may detect biomarkers in saliva (e.g., salivary biomarkers) and form corresponding sensor information which may be further analyzed using any suitable method by a controller of the system to obtain results of the analysis. In accordance with some embodiments, biomarkers may be obtained by a sensor of the system and thereafter analyzed to detect, for example, heart disease using any suitable method. Illustratively, inflammatory biomarkers can be used to detect cardiovascular diseases. For example, the biomarkers may be analyzed to detect health conditions, diseases, etc. (e.g., heart condition, AIDs, etc.).

Further, embodiments, of the present system may include sensors to determine medication adherence (e.g., the sensors may detect consumption of a target medication (e.g. a prescribed medication) which information may be used by the system to determine whether a user properly scheduled his or her medication), eating patterns (e.g., using microphones), snoring (e.g., using microphones), sleep apnea (e.g., using microphones), etc. It is further envisioned that embodiments of the present system may determine whether a user has consumed certain target substances such as alcohol, drugs, or the like. Thus, embodiments of the present system may detect whether a user has consumed a certain target substance (as may be programmed by the system and/or detected by the sensors).

In accordance with some embodiments, the sensor information may be obtained once at a desired time or a plurality of times (e.g. periodically or non-periodically) and may be stored in the memory 154 for later use. For example, temperature information may be sensed by the temperature sensor once every hour between brushes and stored in the memory 154 so that it may be transferred to the PCA 107 when communication with the PCA 107 is established such as during a data acquisition mode. Similarly, audio information may be sampled (e.g., with a desired duration such as a 20 second interval) from the microphone and stored in the memory 154 until being transferred to the PCA 107. In accordance with some embodiments, all desired sensor information may be stored in the memory 154 until it is transferred to the PCA 107 at which time it may be deleted, if desired. However, in yet other embodiments, sensor information may be stored in the memory 154 until being overwritten by more recent sensor information. Thus, sensor information may be stored using a loop method.

In accordance with some embodiments, the sensor information may be obtained when a certain qualifying event is detected (e.g., is determined to occur). For example, the controller 150 may sample the sensor information (e.g., continuously, semi-continuously, periodically, and/or non-periodically) and determine whether a certain qualifying event has occurred. Accordingly, when it is determined that the qualifying event has occurred, the controller may perform one or more actions (e.g., as may be determined by the system and/or user, etc.). For example, if it is determined that an amplitude of the audio information exceeds a corresponding threshold, the corresponding information (e.g., a 20 second audio clip) may be stored in the memory 154 for later use. In accordance with yet other embodiments, when the audio information is determined to match a certain acoustic pattern (e.g., an audio pattern indicative of a user grinding his or her teeth, etc. as may be set by the system and/or user), the controller may control the at least one microphone to sample audio information (e.g., a 20 second clip collected periodically every 3 minutes for the next hour, etc.). Then, this information may be stored in the memory 154 for later use. Various qualifying events and actions to perform when the event is determined to occur (or not occur in some cases depending on settings) may be set by the user and/or system and stored in the memory 154 for later use.

In accordance with some embodiments, the sensor information obtained from at least one sensor of a corresponding tooth portion 112 may be stored with corresponding meta information such as time stamp information, sensor ID, etc. For example, tooth pressure, temperature, and/or audio information may be stored with a corresponding time stamp. In accordance with some embodiments, the sensor information may be overwritten when new sensor information is generated by the sensors.

The base 132 may further include controller 160 which may control the overall operation of the base 132, a memory 164 which may store information generated and/or obtained by the base 132, and at least one antenna 166 which may transmit and/or receive information respectively to and/or from either or both of the PCA 107 and/or the network 110. However, in yet other embodiments, the base 132 may communicate with the network 110 using any suitable wired and/or wireless method(s). For example, the base 132 may communicate with the PCA 107 (e.g., wirelessly via antennas 166 and 126) to obtain sensor information which the PCA 107 obtains from the tooth portion 112. In accordance with some embodiments, the processor 160 of the base 132 may then process the sensor information such as by encrypting the sensor information and thereafter transmit the sensor information to the server 102 for further processing.

Further, in accordance with some embodiments, the base 132 may obtain programming information (e.g., to set parameters, etc.) for the tooth portion 112 from the server 102 (e.g., via the network 110) and may transmit this programming information to the PCA 107 using any suitable wired or wireless communication method or methods. If it is determined that the programming information cannot be transmitted to the PCA 107 (e.g., such as when the PCA 107 is not in or near the base 132 such as when the PCA 107 is in use), the base 132 may store the programming information in the memory 164 until it may be transferred to the PCA 107, such as when the PCA 107 is determined to be in a charging position or charging, depending upon setting. Thus, in accordance with some embodiments, upon receiving the programming information, the PCA 107 may store the programming information in the memory 124 until it may be transferred to the tooth portion 112 such as during the next tooth brushing operation.

In accordance with some embodiments, one or more of the above-described functions of the base 132 may be performed by the PCA 107. However, the base 132 may continue to provide an electromagnetic field suitable to charge the PCA 107.

Communications between the PCA 107 and the tooth portion 112 may be performed using one or more corresponding wireless communication methods. These methods may include proprietary and/or conventional communication methods such as a Bluetooth™ method, a radio-frequency identification (RFID) method or the like operating in accordance with embodiments of the present system. To conserve resources, the desired communication method may include any suitable low-energy wireless communication method or methods, if desired.

With regard to the tooth portion 112, the at least one sensor 152 may sense information and form corresponding sensor information which may be suitable for analysis. For example, the tooth portion 112 may collect audio information from within mouth of a user and may form corresponding audio information (which may form at least a portion of the sensor information of the tooth portion 112). This audio information may be suitable for analysis (e.g., by the server 102) to determine whether the user suffers from sleep apnea. For example, breathing interruption(s) such as sleep apnea can be detected by analyzing the audio information which includes an audio signal. If the system detects an audio signal amplitude that is less than or equal to a threshold value (e.g., an apnea threshold value), the system may determine that the user has sleep apnea. However, if the system detects an audio signal amplitude that is not less than or equal to a threshold value (e.g., an apnea threshold value), the system may determine that the user does not have sleep apnea. Accordingly, audio information may be sampled by the audio sensor over one or more time intervals (e.g., a duration of 30 seconds) as may be set by the user and/or system and corresponding sensor information may be formed. The tooth portion 112 may collect this information at certain periodic and/or non periodic intervals as may be set by the system and/or user. The tooth portion 112 may include a clock which may be used to determine when to acquire the sensor information. For example, audio information for analyzing a sleep pattern of the user may be acquired during expected sleep hours of the user (which may be set by the system and/or user), if desired.

Figure 2:
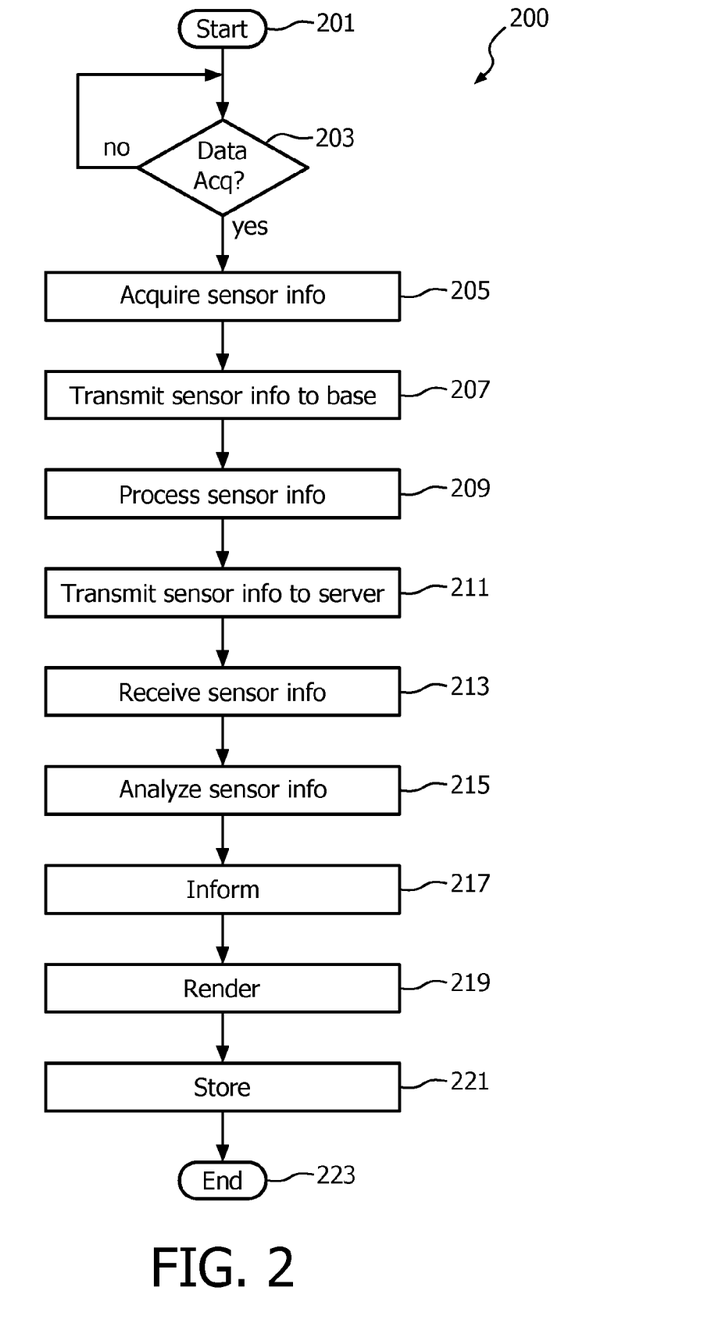
FIG. 2 is a flow diagram that illustrates a process performed by an electronic oral care system in accordance with embodiments of the present system.

FIG. 2 is a flow diagram that illustrates a process 200 performed by an electronic oral care system in accordance with embodiments of the present system. The process 200 may be performed using one or more computers communicating over a network and may obtain information from, and/or store information to one or more memories which may be local and/or remote from each other. The process 200 can include one of more of the following acts. Further, one or more of these acts may be combined and/or separated into sub-acts, if desired. Further, one or more of these acts may be skipped depending upon settings. In operation, the process may start during act 201 and then proceed to act 203.

During act 203, the process may determine whether a data acquisition mode is activated. The data acquisition mode may be activated when the PCA 107 is turned on in which case the actuator 135 is driven by the controller 122. However, in yet other embodiments, the process may determine to activate the data acquisition mode when, for example, it is determined that pressure is applied to the tool 111. In the latter case the PCA 107 may be turned on or off as may be set by the system and/or user. Accordingly, if it is determined that the data acquisition mode is activated, the process may continue to act 205. However, if it is determined that the data acquisition mode is not activated, the process may repeat act 203. In accordance with some embodiments, a user may select to activate the data activation mode manually using a user interface of the system, if desired.

During act 205, the process may control the PCA 107 to acquire sensor information from the tooth portion 112. This process may be performed in accordance with a suitable wireless communication method. For example, if an RFID communication method is being used, the PCA 107 may act as an interrogator (e.g., reader) and transmit information to interrogate the tooth portion 112 in accordance with a selected RFID communication method. However, in accordance with yet other embodiments, the PCA 107 may establish a two-way communication channel with the tooth portion 112 and may use a query-response method to obtain the sensor information from the tooth portion 112. Once the sensor information is obtained by the PCA 107 from the tooth portion 112, the PCA 107 may store the sensor information in the memory 124 until the sensor information may be transferred from the PCA 107 to the base 132. After completing act 205, the process may continue to act 207.

During act 207, the process may control the PCA 107 to transmit the sensor information to the base 132 for further processing. This act may be performed wirelessly once the sensor information is received or may be performed when, for example, a qualifying event is determined to occur. For example, in accordance with some embodiments a qualifying event may include a charging operation of the PCA 107. Accordingly, in accordance with some embodiments, the process may determine if the PCA 107 is being charged and may transfer the sensor information to the base if it is determined that the PCA 107 is being charged. However, if it is determined that the PCA 107 is not being charged, the process may repeat the determination. Further, in accordance with yet other embodiments, the sensor information may be transferred to the base 132 when a user inputs a request to do so on a user interface of the system such as the UI 128. For example, the user may select a data transmission menu item and the PCA 107 may then transmit the sensor information to the base 132. In accordance with some embodiments, the sensor information may be transferred from the PCA 107 to the base 132 using any suitable wired or wireless method or methods. After completing act 207, the process may continue to act 209.

During act 209, the process may control the base to further process the received sensor information. During this processing, for example, the process may encrypt the sensor information in accordance with a desired encryption method. Further, the processing may combine (e.g., consolidate) sensor information from a plurality of tooth sensors 112 which may be associated with (e.g., implanted in) a corresponding user. Thus, for example, if a user has three tooth portions 112 each of which has a different type of sensor (e.g., a microphone, a pressure/force/stress sensor, and a temperature sensor), the sensor information from each of these sensors may be consolidated and associated with the user. Further, the process may add identification information to identify a source (e.g., the user) of the sensor information (e.g., a user's name, account name, etc.), if desired. In yet other embodiments, the sensor information may be unencrypted, if desired, and other transmission methods may be used to ensure data privacy, if desired. After completing act 209, the process may continue to act 211.

During act 211, the base may transmit the processed sensor information to a server of the system (e.g., 102) for further processing. The base may communicate with the server using any suitable communication network such as the Internet, etc. Further, the base may be coupled to the network using any suitable wired and/or wireless communication method such as a wireless fidelity (WiFi) or the like. After completing act 211, the process may continue to act 213. In accordance with some embodiments, one or more actions performed by the base may be performed by the PCA 107. Accordingly, the PCA may include a processor which may prepare the sensor information for transmission and/or a communication portion which may transmit the sensor information to the server 102 for further processing as will be described below.

During act 213, the server may receive the sensor information and thereafter analyze the received sensor information. If the sensor information is encrypted, the server may decrypt the sensor information to extract the sensor information. After completing act 213, the process may continue to act 215.

During act 215, the process may analyze the received and/or extracted sensor information. Further, the process may perform a further extraction process to extract various information which may be included in the sensor information. For example, meta information such as ID information may be extracted from the sensor information to identify a user and/or an account of a user. Similarly, time stamp information may be extracted from the sensor information to identify a time period during which the information was formed by a corresponding sensor. Further, if more than one type of information (e.g., temperature and audio) is included in the sensor information, the process may extract the corresponding types of information for further analysis. With regard to the ID information which may be included in the sensor information, the server may associate the sensor information with an ID of a user associated with the sensor information. Accordingly, the server may obtain stored information associated with the an account of the user which may be previously stored in the memory 105 such as desired tests, previous sensor information (for comparison, etc.), a medical professional associated with the user (e.g., the user's doctor), a contact address (e.g., email address, etc.) associated with the user and/or medical professional associated with the user, etc.

In accordance with some embodiments, the server may determine a type of the sensor information (e.g., audio information, pressure information, temperature information) and may thereafter process the sensor information accordingly. The process may then log the results of the analysis in a memory of the system for later use. The process may also perform tests on the sensor information based upon the users account information and/or determinations from the current test. For example, if a first condition is found (e.g., tooth grinding), the process may then attempt to perform a second related test (a temperature test to determine whether the grinding occurs because the user is consuming food, etc.) using, for example, sensor information from other sensors or types of sensors. After completing act 215, the process may continue to act 217.

During act 217, the process may inform a registered party (e.g., the user, a professional such as a doctor, etc.) of the results of the analysis performed during act 215. The process may perform this act using any suitable method. For example, in accordance with some embodiments, the server may transmit the results of the analysis to the PCA 107 which provided the sensor information. However, in yet other embodiments, the process may transmit a message including results of the analysis to one or more registered addresses such as email address of the user, an address of the registered medical professional (e.g., a doctor, etc.) associated with the user's account, an Internet protocol (IP) address of one or more portions of the system such as the PCA, the base or portions thereof, etc. After completing act 217, the process may continue to act 219.

During act 219, the process may render the results of the analysis on a user interface of the system such as a display, a speaker, etc., of the system. The process may further generate a user interface with which a user may interact to make one or more choices or selections. For example, the process may provide a menu selection items (e.g., menu items, etc.) for a user to select to transmit the results to a medical professional associated with and/or selected by the user. After completing act 219, the process may continue to act 221.

During act 221, the process may store information generated by the process such as the sensor information, the result(s) of the analysis, user inputs or selections, etc., in association with an account of the user in a memory of the system such as the memory 105 for later use. Accordingly, the stored information may be obtained at a later time from the memory 105 and further processed, analyzed, reviewed by a medical professional, etc. Further, the process may update existing information such as previous results (e.g., results obtained during a previous test) corresponding to the user. After completing act 221, the process may continue to act 223 where it ends.

Figure 3:
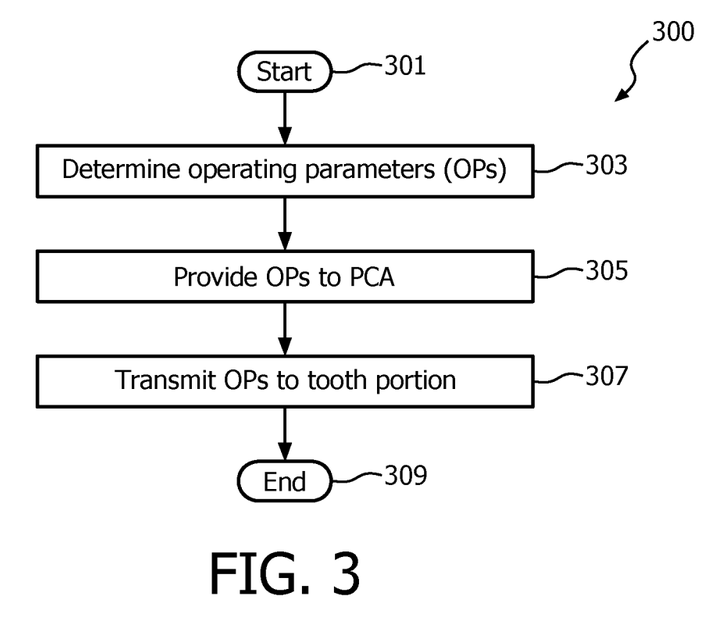
FIG. 3 is a flow diagram that illustrates a process performed by an electronic oral care system in accordance with embodiments of the present system.

FIG. 3 is a flow diagram that illustrates a process 300 performed by a system in accordance with embodiments of the present system. The process 300 may be performed using one or more computers communicating over a network and may obtain information from, and/or store information to one or more memories which may be local and/or remote from each other. The process 300 can include one of more of the following acts. Further, one or more of these acts may be combined and/or separated into sub-acts, if desired. Further, one or more of these acts may be skipped depending upon settings. In operation, the process may start during act 301 and then proceed to act 303.

During act 303, the process may determine operating parameters for the smart tooth. The operating parameters may set forth for example, one or more of types of sensor information to obtain, times when the corresponding type of sensor information may be obtained, duration, and/or qualifying events (e.g., sensed temperature is determined to be greater 110 degrees, etc.) and acts to perform when qualifying events are determined to occur (e.g., detected). The operating parameters may be set by a user (e.g., a patient, a medical professional, etc.) and/or system. For example, the process may generate a user interface (e.g., at the UI 190 and/or PCA 107) with which a user may interact to make set/reset one or more operating parameters as desired. Accordingly, a medical professional may remotely set/reset (e.g., change) one or more operating parameters, as desired. However, it is also envisioned that the process (e.g., the server 102) may set/reset one or more operating parameters in accordance with, for example, results of the analysis or other determinations of the system, sensor information, and/or system rules. For example, if a user is determined to be grinding his or her teeth, the process may request audio information to be collected from the sensors of the tooth portion. In yet other embodiments, a user may desire to collect audio information, etc. In accordance with yet other embodiments, default operating parameters may be set by the system. After completing act 303, the process may continue to act 305.

During act 305, the operating parameters set/reset by the system and/or user may be provided to the PCA via any suitable communication method. For example, operating parameters determined by the server may be transmitted to the PCA via the network directly (if the PCA has communication capabilities) or via the base. Then, for example, the base may provide the operating parameters to the PCA when, for example, the PCA is coupled to the base for charging, etc. The PCA may store the operating parameters it obtains in its memory (e.g., the memory 124) for later use and/or transmission to the tooth portion. In accordance with some embodiments, the PCA may analyze the operating parameters and separate operating parameters for the PCA from those for the tooth portion. After completing act 305, the process may continue to act 307.

During act 307, the process may transmit the operating parameters to the tooth portion 112 and the tooth portion may apply the received operating parameters. Accordingly, the tooth portion 112 may update its operating parameters in accordance with received (e.g., current) operating parameters and may store the (current) operating parameters in its memory for later use. Further, the process may configure the controller of the tooth portion (e.g., 150) in accordance with the obtained operating parameters for future use. In accordance with some embodiments, the process may transmit the operating parameters when it is determined that the data acquisition mode is activated as set forth during act 203. After completing act 307, the process may continue to act 309, where it ends.

While the present invention has been shown and described with reference to particular exemplary embodiments, it will be understood by those skilled in the art that present invention is not limited thereto, but that various changes in form and details, including the combination of various features and embodiments, may be made therein without departing from the spirit and scope of the invention.

Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, the section headings included herein are intended to facilitate a review but are not intended to limit the scope of the present system. Accordingly, the specification and drawings are to be regarded in an illustrative manner and are not intended to limit the scope of the appended claims.

The section headings included herein are intended to facilitate a review but are not intended to limit the scope of the present system. Accordingly, the specification and drawings are to be regarded in an illustrative manner and are not intended to limit the scope of the appended claims.

In interpreting the appended claims, it should be understood that: the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same item or hardware or software implemented structure or function; any of the disclosed elements may be comprised of hardware portions (e.g., including discrete and integrated electronic circuitry), software portions (e.g., computer programming), and any combination thereof; hardware portions may be comprised of one or both of analog and digital portions; any of the disclosed devices or portions thereof may be combined together or separated into further portions unless specifically stated otherwise; no specific sequence of acts or steps is intended to be required unless specifically indicated; the term "plurality of" an element includes two or more of the claimed element, and does not imply any particular range of number of elements; that is, a plurality of elements may be as few as two elements, and may include an immeasurable number of elements; and the term and/or and formatives thereof should be understood to mean that only one or more of the listed elements may need to be suitably present in the system in accordance with the claims recitation and in accordance with one or more embodiments of the present system.

What is claimed is:

1. A personal care system, comprising:
   at least one tooth-based sensor adapted to be coupled to a surface within a user's mouth and capable of sensing information;
   at least one of a remote server or a base portion and;
   a personal care apparatus (PCA) having a body with at least one cavity, the body configured to receive a cleaning tool at a second end and having at least one controller situated within the at least one cavity which is configured to:
   determine whether an operating mode is activated,
   obtain sensor information from the at least one tooth-based sensor, and when it is determined that the operating mode is activated,
   transmit the sensor information to at least one of the remote server or the base portion.

2. The system of claim 1, wherein the tooth-based sensor is capable of sensing information related to at least one of temperature, ph level, bacterial levels, presence of a target bacterium, audio information, force information, and glucose level.

3. The system of claim 1, wherein the at least one controller is further configured to establish communication with the at least one tooth-based sensor using a low-energy wireless communication method.

4. The system of claim 1, wherein the at least one controller transmits the sensor information to the base portion when it is determined that a charging mode is activated.

5. The system of claim 1, wherein the base portion, if present, is configured to receive the sensor information and transmit the sensor information to the remote server.

6. The system of claim 1, wherein the remote server, if present, further comprises at least one processor configured to receive the transmitted sensor information and analyze the sensor information.

7. The system of claim 6, wherein the remote server further transmits results of the analysis to at least one registered address of a user.

8. A method of obtaining sensor information, the method performed by at least one controller of the personal care apparatus and comprising acts of:
   providing a personal care apparatus having a body with at least one actuator and an oral cleaning tool coupled to the at least one actuator,
   providing a tooth-based sensor that is coupled to a surface within a user's mouth that senses information within the user's mouth,
   determining whether an operating mode is activated,
   obtaining sensor information from the at least one tooth-based sensor, when it is determined that the operating mode is activated; and
   transmitting the sensor information to at least one of a remote server and a base portion.

9. The method of claim 8, wherein the sensor information comprises information related to at least one of temperature, ph level, bacterial levels, presence of a target bacterium, audio information, force information, and glucose level.

10. The method of claim 8, further comprising an act of establishing communication with the at least one tooth-based sensor using a low-energy wireless communication method.

11. The method of claim 8, wherein the act of transmitting the sensor information to the base portion is performed when it is determined that a charging mode is activated.

12. The method of claim 8, wherein the act of transmitting the sensor information further comprising acts of:
   receiving the sensor information at the base portion; and
   transmitting, by the base portion, the sensor information to the remote server.

13. The method of claim 8, further comprising an act of analyzing the sensor information by the remote server.

14. The method of claim 13, further comprising an act of transmitting, by the remote server, results of the analysis to at least one registered address of a user.

* * * * *